United States Patent
Abate et al.

(10) Patent No.: US 11,116,886 B2
(45) Date of Patent: Sep. 14, 2021

(54) ACCESSORY FOR A NASAL MUCOUS ASPIRATOR, NASAL ASPIRATOR AND KIT

(71) Applicant: OMRON HEALTHCARE CO., LTD., Muko (JP)

(72) Inventors: Giorgio Abate, Brescia (IT); Simone Abate, Brescia (IT); Davide Fraccaroli, Brescia (IT)

(73) Assignee: OMRON HEALTHCARE CO., LTD., Kyoto (JP)

( * ) Notice: Subject to any disclaimer, the term of this patent is extended or adjusted under 35 U.S.C. 154(b) by 568 days.

(21) Appl. No.: 16/104,279

(22) Filed: Aug. 17, 2018

(65) Prior Publication Data

US 2018/0369459 A1    Dec. 27, 2018

Related U.S. Application Data

(63) Continuation of application No. PCT/IT2016/000041, filed on Feb. 18, 2016.

(51) Int. Cl.
*A61M 1/00*    (2006.01)
*A61M 15/08*    (2006.01)
(Continued)

(52) U.S. Cl.
CPC .......... *A61M 1/804* (2021.05); *A61M 1/0003* (2013.01); *A61M 11/02* (2013.01);
(Continued)

(58) Field of Classification Search
CPC .... A61M 1/00; A61M 1/0003; A61M 1/0039; A61M 1/0076; A61M 1/008;
(Continued)

(56) References Cited

U.S. PATENT DOCUMENTS 2,485,184 A    10/1949  Blackman et al.
2,546,214 A *   3/1951  Curry .................... A61M 11/06
                                            128/200.21
(Continued)

FOREIGN PATENT DOCUMENTS

CN    102307553 A    1/2012
CN    102753228 A    10/2012
(Continued)

OTHER PUBLICATIONS

Official Communication issued in International Patent Application No. PCT/IT2016/000041, dated Nov. 10, 2016.
(Continued)

*Primary Examiner* — Kendra D Carter
*Assistant Examiner* — Thomas W Greig
(74) *Attorney, Agent, or Firm* — Keating & Bennett, LLP (57) ABSTRACT

An accessory for a nasal mucus aspirator includes an accessory body suitable to be gripped and a terminal nozzle placed at a distal end of said accessory body and suitable to be at least partially inserted into a nostril of a user. In the accessory body, there are formed a compressed air inlet passage suitable to be fluidically connected to a compressed air source for receiving a flow of air at a positive pressure, said compressed air inlet passage defining a constriction so as to generate a Venturi effect, and an aspiration duct flowing into said constriction and fluidically connected to the terminal nozzle so as to generate a negative pressure due to the Venturi effect suitable to aspirate the mucus.

20 Claims, 7 Drawing Sheets

(51) Int. Cl.
*A61M 11/02* (2006.01)
*A61M 11/06* (2006.01)

(52) U.S. Cl.
CPC .............. *A61M 15/08* (2013.01); *A61M 11/06* (2013.01); *A61M 2205/70* (2013.01); *A61M 2205/8206* (2013.01); *A61M 2209/06* (2013.01); *A61M 2210/0618* (2013.01); *A61M 2210/0625* (2013.01); *A61M 2240/00* (2013.01)

(58) Field of Classification Search
CPC .. A61M 15/08; A61M 1/0005; A61M 1/0007; A61M 1/0049; A61M 1/0062; A61M 1/0031; A61M 1/0066
See application file for complete search history.

(56) References Cited

U.S. PATENT DOCUMENTS

| | | | |
|---|---|---|---|
| 5,788,683 | A | 8/1998 | Martin |
| D689,185 | S | 9/2013 | Flickinger et al. |
| 2002/0170928 | A1 | 11/2002 | Grychowski et al. |
| 2008/0312674 | A1* | 12/2008 | Chen .................. A61M 1/0058 606/162 |
| 2009/0076441 | A1* | 3/2009 | Sebban ............... A61M 3/0208 604/35 |
| 2010/0233654 | A1 | 9/2010 | Yang |
| 2011/0132354 | A1 | 6/2011 | Flickinger et al. |
| 2011/0137290 | A1 | 6/2011 | Flickinger et al. |
| 2012/0000460 | A1 | 1/2012 | Flickinger |
| 2012/0152238 | A1 | 6/2012 | Flickinger et al. |
| 2012/0160237 | A1 | 6/2012 | Flickinger |
| 2013/0289504 | A1* | 10/2013 | Esnouf ................ A61M 1/0031 604/320 |
| 2013/0310747 | A1 | 11/2013 | Lambert |
| 2014/0093841 | A1 | 4/2014 | Yang |
| 2014/0283820 | A1 | 9/2014 | Flickinger et al. |
| 2015/0126927 | A1 | 5/2015 | Flickinger |
| 2016/0279305 | A1* | 9/2016 | Esnouf ................ A61M 1/0074 |
| 2016/0339188 | A1 | 11/2016 | Flickinger |
| 2017/0028144 | A1 | 2/2017 | Flickinger |

FOREIGN PATENT DOCUMENTS

| | | |
|---|---|---|
| CN | 103533968 A | 1/2014 |
| JP | 2011-518577 A | 6/2011 |
| WO | 2006/118064 A1 | 11/2006 |
| WO | 2009/051367 A1 | 4/2009 |
| WO | 2010/089789 A1 | 8/2010 |

OTHER PUBLICATIONS

Official Communication issued in corresponding Japanese Patent Application No. 2018-543711, dated Dec. 24, 2019.
Official Communication issued in corresponding Chinese Patent Application No. 201680082000.8, dated Aug. 4, 2020.

\* cited by examiner

FIG.8

ACCESSORY FOR A NASAL MUCOUS ASPIRATOR, NASAL ASPIRATOR AND KIT

CROSS REFERENCE TO RELATED APPLICATIONS

This application is a Continuation Application of PCT Application No. PCT/IT2016/000041 filed on Feb. 18, 2016. The entire contents of this application are hereby incorporated herein by reference.

BACKGROUND OF THE INVENTION

1. Field of the Invention

This invention relates to an accessory for a nasal mucus aspirator, an aspirator and a kit that use this accessory.

2. Description of the Related Art

The nasal aspirator is used and recommended by paediatricians for diseases related to the production of mucus from the nose in children. The small child, not being able to blow its nose, it needs to be cleaned frequently to ensure that mirror inflammatory conditions do not become more serious. For this purpose, it is usually damp the baby's nose with physiological water (e.g., 0.9% isotonic or hypertonic NaCl) and subsequently the nasal aspirator is used to remove the mucus, ensuring the child a proper breathing, resulting in peaceful sleep and prevention of the most important inflammatory diseases.

There are currently different types of nasal mucus aspirators.

For example, mouth aspirators are widespread, in which, to aspirate the mucus from the child, there is a tube which is held in the adult's mouth and which terminates with a nozzle that goes in contact with the mucus to be aspirated. The adult sucks from the mouth and the mucus ends in the nozzle.

These mouth aspirators are inexpensive and do not require energy to operate but have the disadvantage of contaminating the operator, because the microbes are sucked at the time of use and end up directly in the mouth of the person who performs the treatment. In addition, the depression created in the child's nostrils depends on the intensity with which the adult sucks the air, and this intensity is sometimes insufficient and sometimes rather excessive with the risk of causing damage to the child.

Electric battery-powered aspirators are also known: they are more effective than mouth aspirators and are transportable, but they are more expensive, noisy and require changing the batteries when discharged.

To overcome the problem of replacing the batteries there are electric aspirators that work with the mains voltage. They are effective, but more cumbersome, are also noisy and have a high cost.

Finally, manual aspirators are known: they are simple, inexpensive and do not need power to operate. However, they are not very effective.

SUMMARY OF THE INVENTION

Preferred embodiments of the present invention provide a nasal mucus aspirator capable of eliminating the drawbacks complained about above with reference to the prior art.

In particular, the invention proposes to make available a mucus aspirator that meets all the safety standards required in medical applications, which does not contaminate the person who performs the treatment, and that, at the same time, has small dimensions and a low cost.

Such objects are achieved with an accessory for a nasal aspirator according to claim 1, with a nasal aspirator according to claim 17, with a kit for the treatment of the upper respiratory system according to claim 18, and with a method for the aspiration of nasal mucus according to claim 19. The dependent claims describe preferred embodiments of the invention.

The above and other elements, features, steps, characteristics and advantages of the present invention will become more apparent from the following detailed description of the preferred embodiments with reference to the attached drawings.

BRIEF DESCRIPTION OF THE DRAWINGS

The characteristics and advantages of the accessory and the nasal mucus aspirator according to the invention will, in any case, be evident from the following description of its preferred embodiments, provided by way of non-limiting examples, with reference to the accompanying figures, in which.

DETAILED DESCRIPTION OF THE PREFERRED EMBODIMENTS

In said drawings, numeral 1 denotes an accessory for a nasal mucus aspirator according to the invention as a whole.

In a general preferred embodiment, the accessory 1 comprises an accessory body 10 suitable to be gripped and a terminal nozzle 12 placed at a distal end of the accessory body 10. The accessory body 12 is suitable to be connected to a compressed air source 200. The terminal nozzle 12 is suitable to be at least partially inserted into a nostril of a user. To this purpose, the terminal nozzle 12 has a tapered shape towards its distal end 12', for example a conical shape.

In the following description, distal end or portion means an end or portion facing towards the terminal nozzle 12, i.e., facing the free end of the accessory 1; proximal end or portion means an end or portion facing towards, or connected to, the compressed air source 200.

The nozzle 12 is formed a terminal of mucus inlet conduit 14. This mucus inlet duct is thus open in correspondence of the distal end 12' of the terminal nozzle 12.

The accessory body 10 has an oblong shape, preferably of circular section. Considering the accessory 10 oriented in a substantially vertical position of use, in a preferred embodiment, the accessory body 10 has a vertical cylindrical lower portion 10' and an upper portion 10" inclined with respect to the vertical axis, so as to increase the ergonomics of the accessory and facilitate the positioning of the distal end 12' of the terminal nozzle 12 in the child's nostril.

In the accessory body 10, a compressed air inlet passage 16 is formed and is suitable to be fluidically connected to the compressed air source 200 to receive a flow of air at a positive pressure. The compressed air inlet passage 16 forms a constriction 16*c* so as to generate a Venturi effect.

In other words, the compressed air passage 16 undergoes a reduction of the section of the flow of compressed air in the direction of advancement of flow, in virtue of which a pressure difference is created between the portion of greater section, in which the flow is at a higher pressure, and the portion of smaller section, i.e., the constriction 16*c*, in which the flow is at a lower pressure.

In the accessory body 10, there is also provided an aspiration duct 20 that flows into the constriction 16*c* and that is fluidically connected to the mucus inlet duct 14.

In a preferred embodiment, the aspiration duct has a proximal chamber 18 that fluidically intercepts the constriction 16*c*.

Thanks to the Venturi effect, and to the fluidic connection between the constriction 16*c*, the aspiration duct 20 and the mucus inlet duct 14, inside the latter generates a negative pressure suitable for the aspiration of the mucus.

More in detail, the compressed air inlet passage 16 comprises a proximal end portion 16*a*, suitable to be connected to the compressed air source 200, a distal portion 16*b* in fluidic communication with the external environment, and the constriction 16*c* between the proximal and distal portions.

The constriction 16*c* has a compressed air passage section smaller at least than the proximal portion passage section 16*a*.

Of course, the proximal-distal indication of the portions of the compressed air inlet passage 16 must not necessarily imply that such passage 16 has an orientation that follows the orientation of the development of the accessory body 10. This orientation of the compressed air inlet passage 16 may be advantageous in terms of limiting the transversal dimensions of the accessory and minimising losses of load, but might also be chosen differently with respect to what is shown in the accompanying drawings.

In a preferred embodiment, in the accessory body 10, there is formed a mucus collection chamber 30 in fluidic communication with the mucus inlet duct 14.

Preferably, the aspiration passage 20 extends externally of the mucus collection chamber 30. In other words, the aspiration passage 20 is fluidically separated from the mucus collection chamber 30, so as to avoid the introduction of mucus in that passage, and therefore its obstruction.

However, it should be noted that, in case of obstruction of the constriction 16*c* due to the presence of mucus in the aspiration duct 20, there is an interruption of the Venturi effect with consequent increase of pressure inside the accessory body. By virtue of this pressure increase, the mucus present in the compressed air inlet passage 16 is expelled through vent openings formed in the accessory body and described later. In other words, working in compression the accessory cleans itself and is then able to restore its aspiration function.

In a preferred embodiment, the mucus inlet duct 14 extends from the distal end 12' of the terminal nozzle 12 along a direction substantially rectilinear and has a proximal end 14' facing an open side of the mucus collection chamber 30.

For example, the mucus collection chamber 30 has a cylindrical shape with a cross section substantially coincident to that of the accessory body 10. Preferably, the mucus collection chamber 30 extends around a chamber axis parallel to the development axis of the mucus inlet duct 14.

Preferably, the proximal end 14' of the mucus inlet duct 14 partially penetrates into the mucus collection chamber 30.

In a preferred embodiment, the aspiration passage 20 has a distal portion 20*b* that extends to the side of and that distally terminates beyond the proximal end 14' of the mucus inlet duct 14, so as to avoid that the mucus coming from this inlet duct 14 might be introduced, in addition to in the mucus collection chamber 30, in the aspiration passage 20.

In accordance with an aspect of the invention, the compressed air inlet passage 16, and a proximal end portion 20*a* of the aspiration passage 20 are formed in a Venturi insert 40 housed in an insert seat 42 formed in the accessory body 10, preferably in a lower portion, or proximal, portion of it.

The Venturi insert 40 is thus a component obtained separately from the accessory body 10, for example in a single piece of plastic material by moulding.

More in detail, the Venturi insert 40 comprises, aligned with each other along an insert longitudinal axis, a proximal portion 40*a* defining a proximal portion 16*a* of the compressed air inlet passage 16 and a distal portion 40*b* defining a distal portion 16*b* of the compressed air inlet passage 16.

The Venturi insert 40 also includes an intermediate portion 40*c* that defines a proximal portion 20*a* of the aspiration passage 20, flowing into the constriction 16*c*, for example with the proximal chamber 18.

In a preferred embodiment, this intermediate portion 40*c* of the Venturi insert extends from the constriction 16*c* along a transverse direction and terminates with a distal end 44 sealingly inserted in an intermediate portion 20*c* of the aspiration passage 20, formed in the accessory body 10. For example, this intermediate portion 20*c* of the aspiration passage 20, and thus the distal end of the intermediate portion 40*c* of the Venturi insert, are parallel to the longitudinal insert axis.

In a preferred embodiment, the distal end 44 of the intermediate portion 40*c* of the Venturi insert 40 is provided with an annular sealing element 46, which cooperates with the side wall that delimits the intermediate portion 20*c* of the aspiration passage 20.

In a preferred embodiment, the Venturi insert 40 is removable from the insert seat 42 through a proximal opening 48 of the accessory body 10.

In a preferred embodiment, the Venturi insert 40 is held in the insert seat 42 thanks to a calibrated interference between the annular sealing element 46 and the side way that delimits the intermediate portion 20*c* of the aspiration passage 20. By virtue of such interference, even after removing the lower closing element of the accessory body, which will be described below, the Venturi insert 40 cannot disengage by gravity from the related insert seat but remains connected there. In other words, removing the Venturi insert 40 to be cleaned or, if necessary, replaced, requires a voluntary manual extraction action by the user.

In a preferred embodiment, the proximal portion 16*a* of the compressed air inlet passage 16 is configured to be sealingly engaged by a fitting 210 connected to a tube 220 from the compressed air source 200. For example, the fitting 210 is suitable to be inserted by pressure in the proximal portion 16*a* of the compressed air inlet passage.

In a preferred embodiment, wherein the proximal end of the accessory body 10 is open and delimits the access opening to the insert seat 42 for the insertion and the extraction of the Venturi insert, to this proximal end of the body of accessory 10 is removably attached a ring nut 50 in which is formed an fitting opening 52 aligned to the proximal portion 16a of the compressed air inlet passage 16 and suitable to allow the passage of the fitting 210 through the ring nut 50.

In a preferred embodiment, the Venturi insert 40 is engaged by the ring nut 50 in such a way that the removal of the Venturi insert 40 from the insert seat 42 is only possible after having disengaged the ring nut 50 from the accessory body 10. The ring nut 50 thus performs the function of retaining the Venturi insert 40 in the related insert seat 42 when the operator removes the fitting 210 by the Venturi insert itself.

In a preferred embodiment, the Venturi insert 40 comprises a ring nut coupling crown 402 provided with coupling means that engage corresponding coupling counter-means formed in an annular portion 502 of the ring nut 50.

For example, the coupling means comprise teeth 404 adapted to engage corresponding openings 504 formed in the annular portion 502.

As stated above, the insert seat 42 is in fluidic communication with the outside environment to avoid the occurrence of a potentially dangerous overpressure in the accessory body 10.

In a preferred embodiment, the ring nut 50 is provided with a bottom wall 51 traversed by vent holes 506 that fluidically connect the insert seat 42 with the outside environment. Additional vent passages can be provided for example between the teeth 404 of the Venturi insert and the openings 504 of the ring nut and/or between the fitting 210 and the fitting opening 52 formed in the ring nut.

Figure 1:
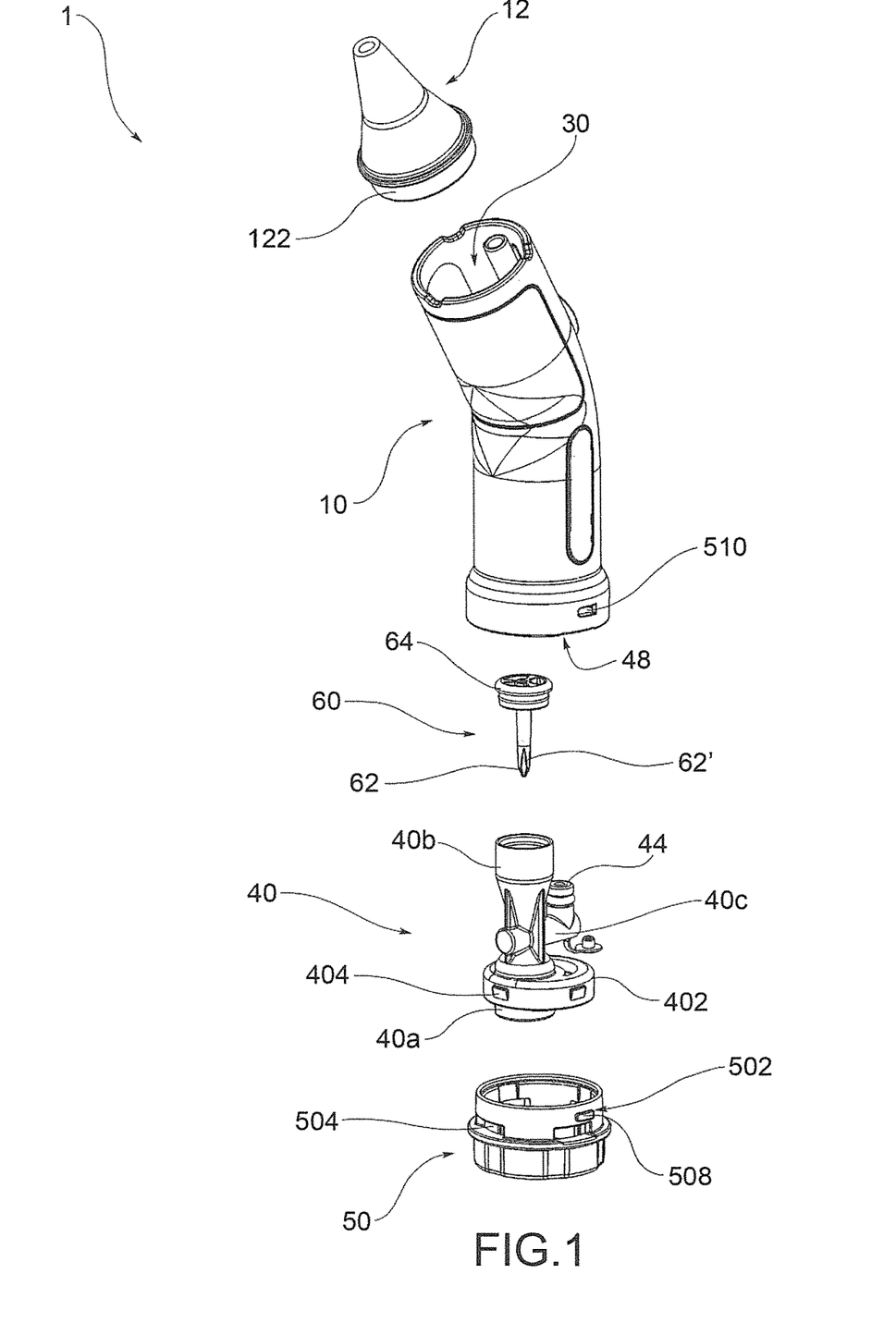
FIG. 1 is an exploded perspective view of the accessory for nasal mucus aspirator according to the present invention.
Figure 2:
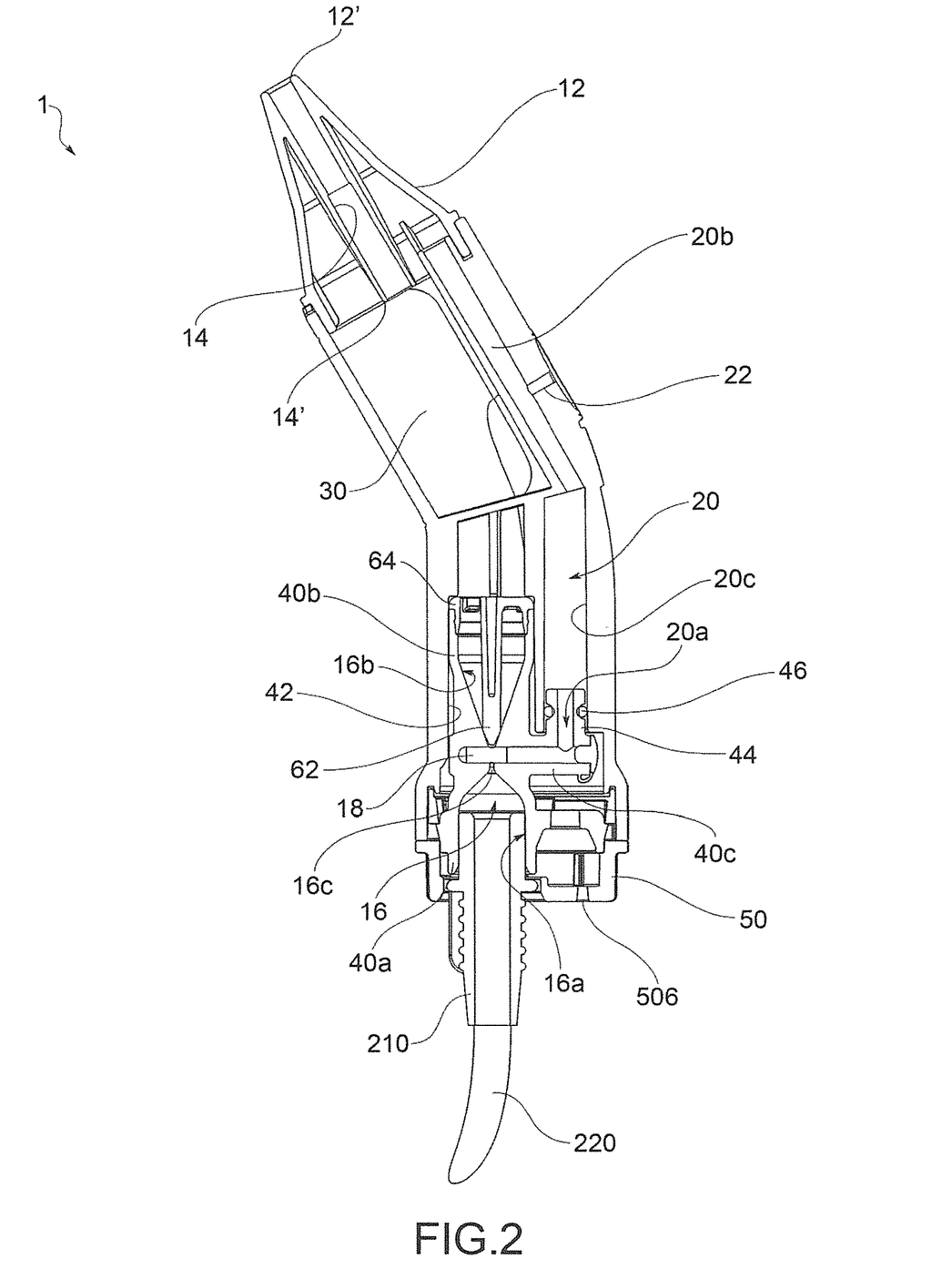
FIG. 2 is a view in axial section of the accessory assembled and connected to a pressurised air supply tube.
Figure 3:
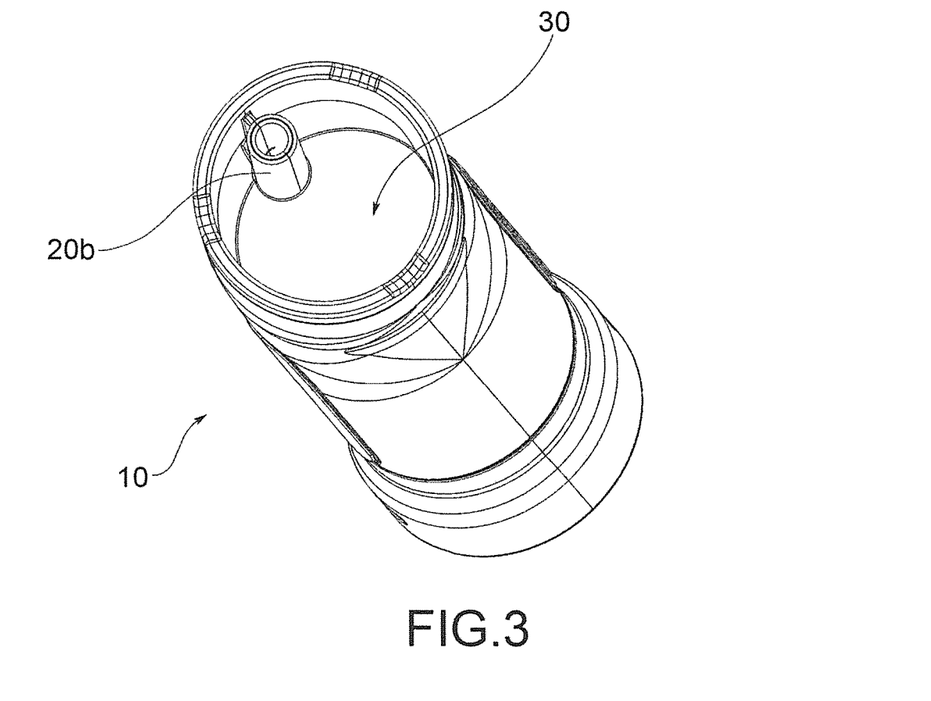
FIG. 3 is a distal end view of only the accessory body.
Figure 4:
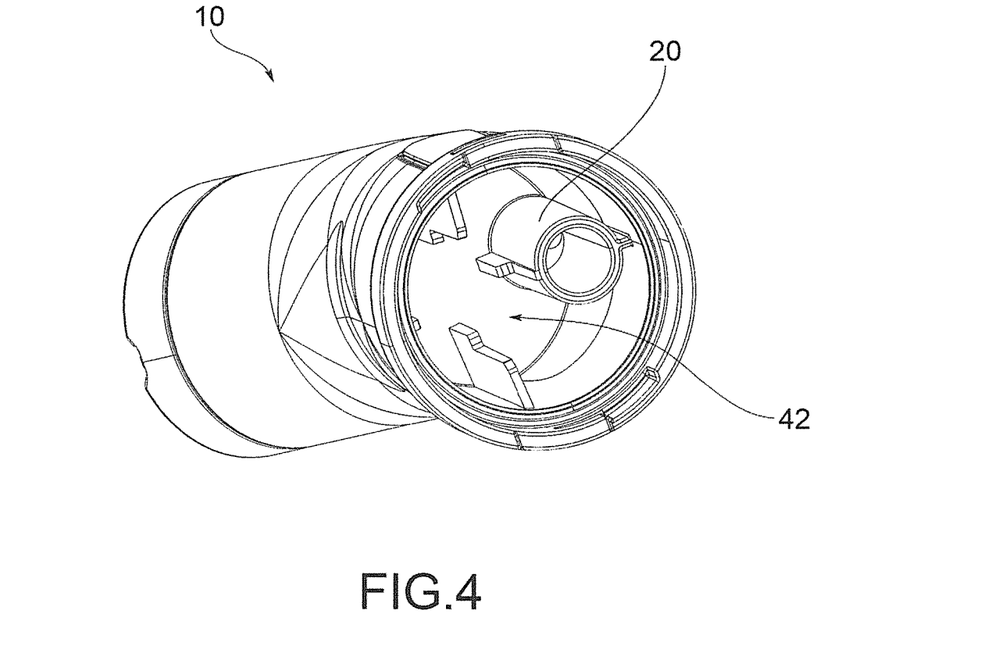
FIG. 4 is a proximal end view proximal of only the accessory body.
Figure 5:
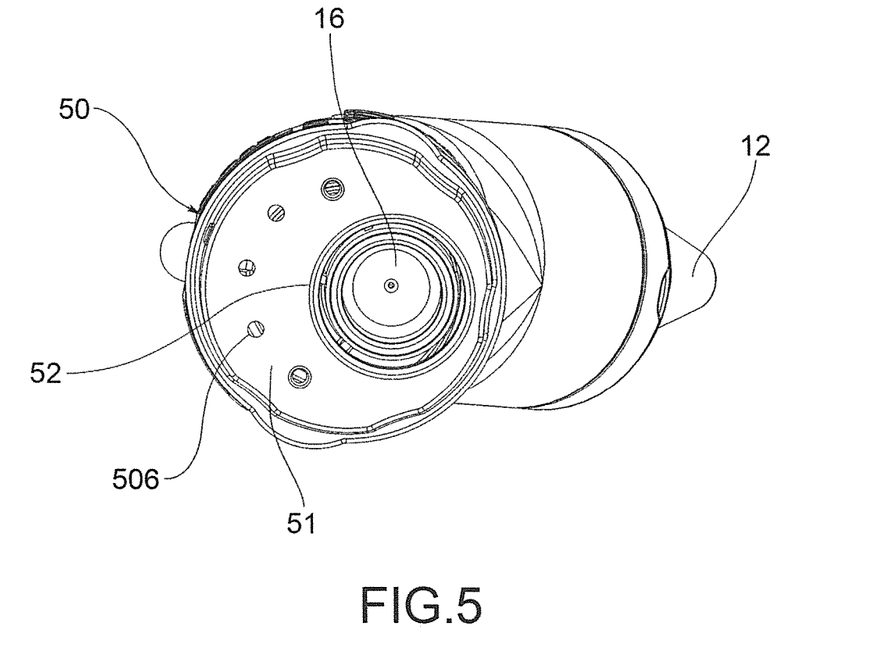
FIG. 5 is a proximal end view of the assembled accessory.
Figure 5A:
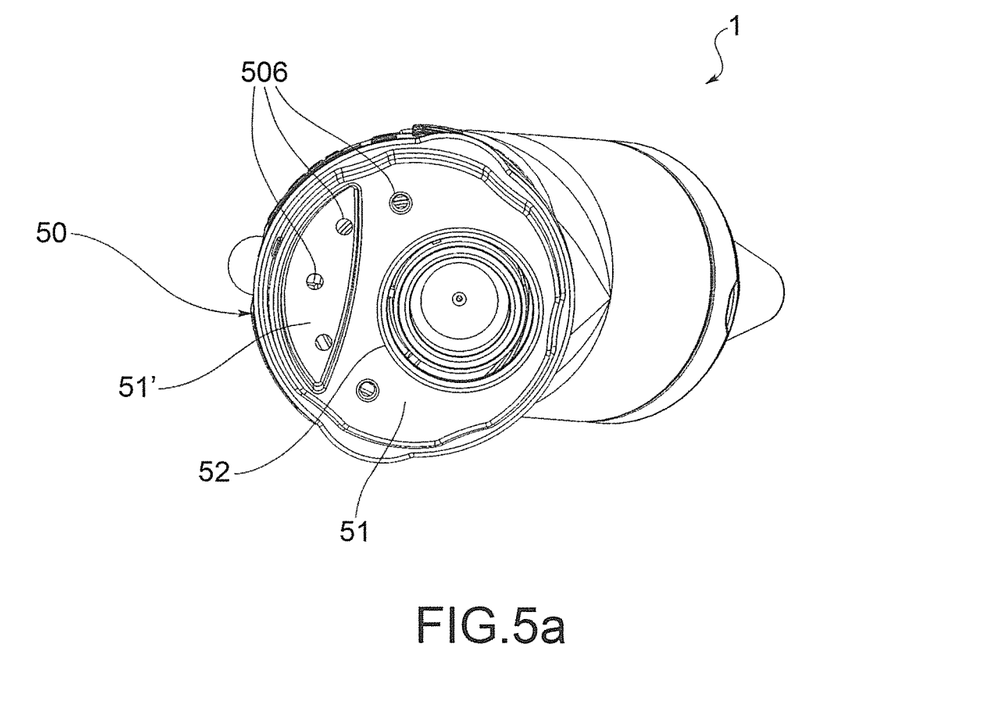
FIG. 5a is a proximal end view of the assembled accessory, in a preferred embodiment variant.
Figure 7:
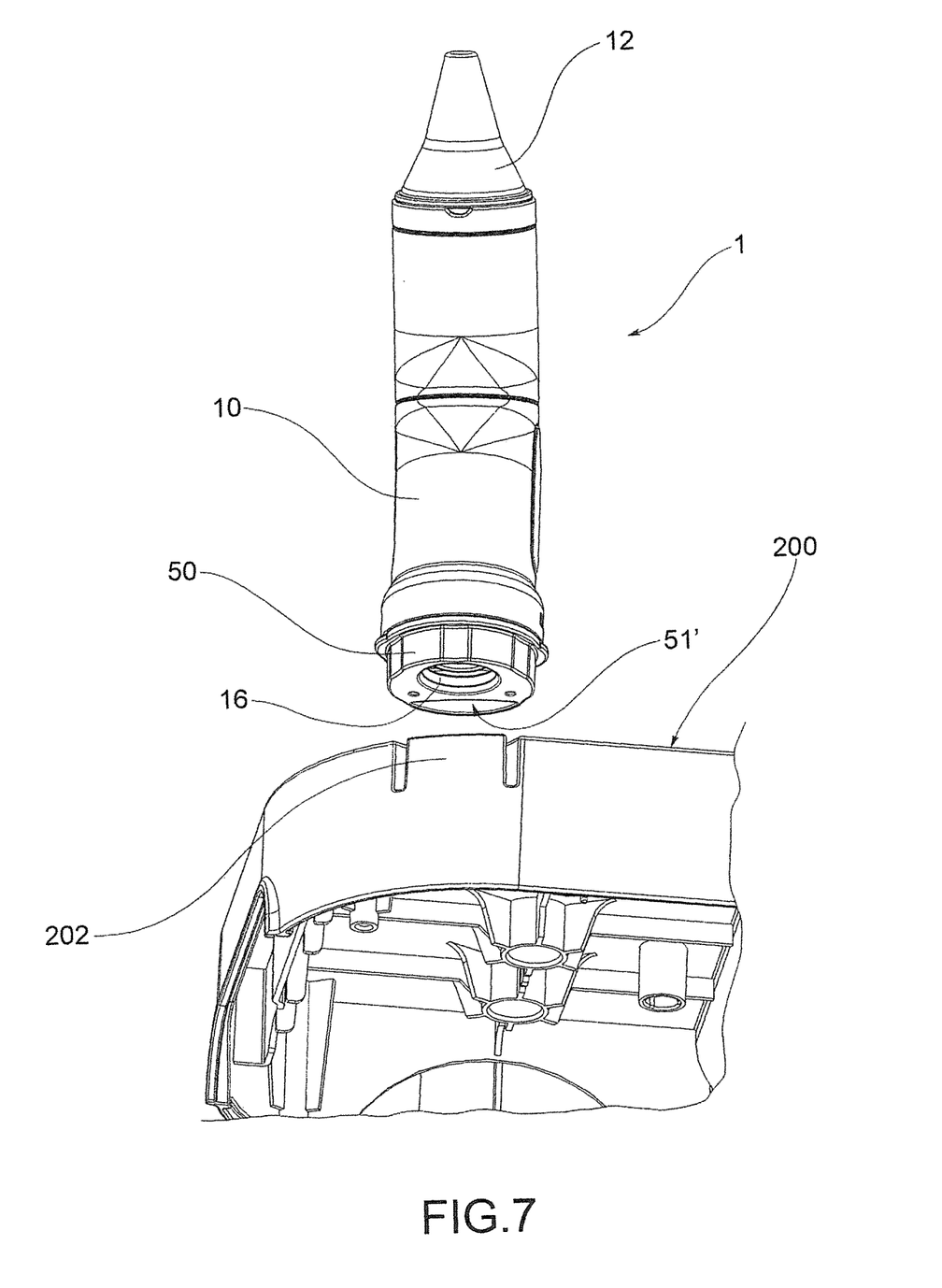
FIG. 7 is a perspective view of the accessory of FIG. 5a in the step of coupling to the body of a compressor.

In a preferred embodiment illustrated in FIG. 5a, the bottom wall 51 includes a recessed 51' portion suitable to receive by shape-coupling a coupling tooth 202 formed in a wall of the body of the compressed-air generator 200, as shown in FIG. 7.

In a preferred embodiment, the ring nut 50 is connected to the accessory body 10 by means of radial projections 508 formed in the annular portion 502 of the ring nut 50 and are suitable to engage corresponding coupling openings 510 formed in the accessory body 10.

In a preferred embodiment, the ring nut 50 is connected to the accessory body 10 by means of a bayonet coupling, which thus requires a rotation of the ring nut 50 with respect to the accessory body 10. In this preferred embodiment, the Venturi insert 40 and the ring nut 50 are connected together with the possibility of a rotation of the ring with respect to the Venturi insert. In this way, even when the Venturi insert is inserted into the accessory body, the ring nut can be rotated with respect to the Venturi insert in a measure such as to allow the connection with bayonet coupling of the ring nut to the accessory body, or their decoupling. For example, the teeth 404 of the Venturi insert have a radial extension less than the corresponding openings 504 formed in the annular portion 502.

In accordance with a further aspect of the invention, the constriction 16c of the compressed air inlet passage 16 is engaged by a pointed end 62 of a peg 60 positioned in the distal portion 16b of the compressed air inlet passage 16.

In a preferred embodiment, such a pointed end 62 of the peg 60 mates geometrically with the tapered end of the distal portion 16b of the compressed air inlet passage 16, facing towards the constriction 16c. To allow the passage of air from the constriction 16c to such distal portion 16b, in the pointed end 62 of the peg 60 are formed longitudinal grooves 62'.

In a preferred embodiment, which provides for the presence of the Venturi insert, the peg 60 has a drilled head 64 that engages the distal end of the distal portion 16b of the compressed air inlet passage 16.

Experimental tests have demonstrated that the presence of the peg 60 amplifies the Venturi effect and also acts as silencer reducing the noise of the device.

In a preferred embodiment, the terminal nozzle 12 is removably coupled to the accessory body 10 by means of calibrated interference between the annular wall of a nozzle base 122 and the side wall of the distal end of the accessory body 10. Preferably, the calibrated interference is chosen in such a way that the terminal nozzle 12 disengages from the accessory body 10 if, in the accessory body, due to an obstruction, a positive pressure is generated higher than a predetermined threshold value, for example between 0.1 and 1 bar.

In a preferred embodiment, to provide a further safety element that prevents the occurrence of an overpressure in the accessory body 10, the fitting 210 and the proximal portion 16a of the compressed air inlet duct 16 are coupled together with a calibrated interference chosen in such a way that, in the presence of a pressure higher than a predetermined threshold value, for example between 0.1 and 1 bar, in the accessory body 10, the fitting 210 is automatically slips off from the compressed air input duct 16.

In a preferred embodiment, the aspiration passage 20 communicates with the external environment through an actuation hole 22 formed in the side wall of the accessory body 10. This actuation hole 22 is suitable to be manually closed by the operator when he wants to start the aspiration of the mucus.

Figure 6:
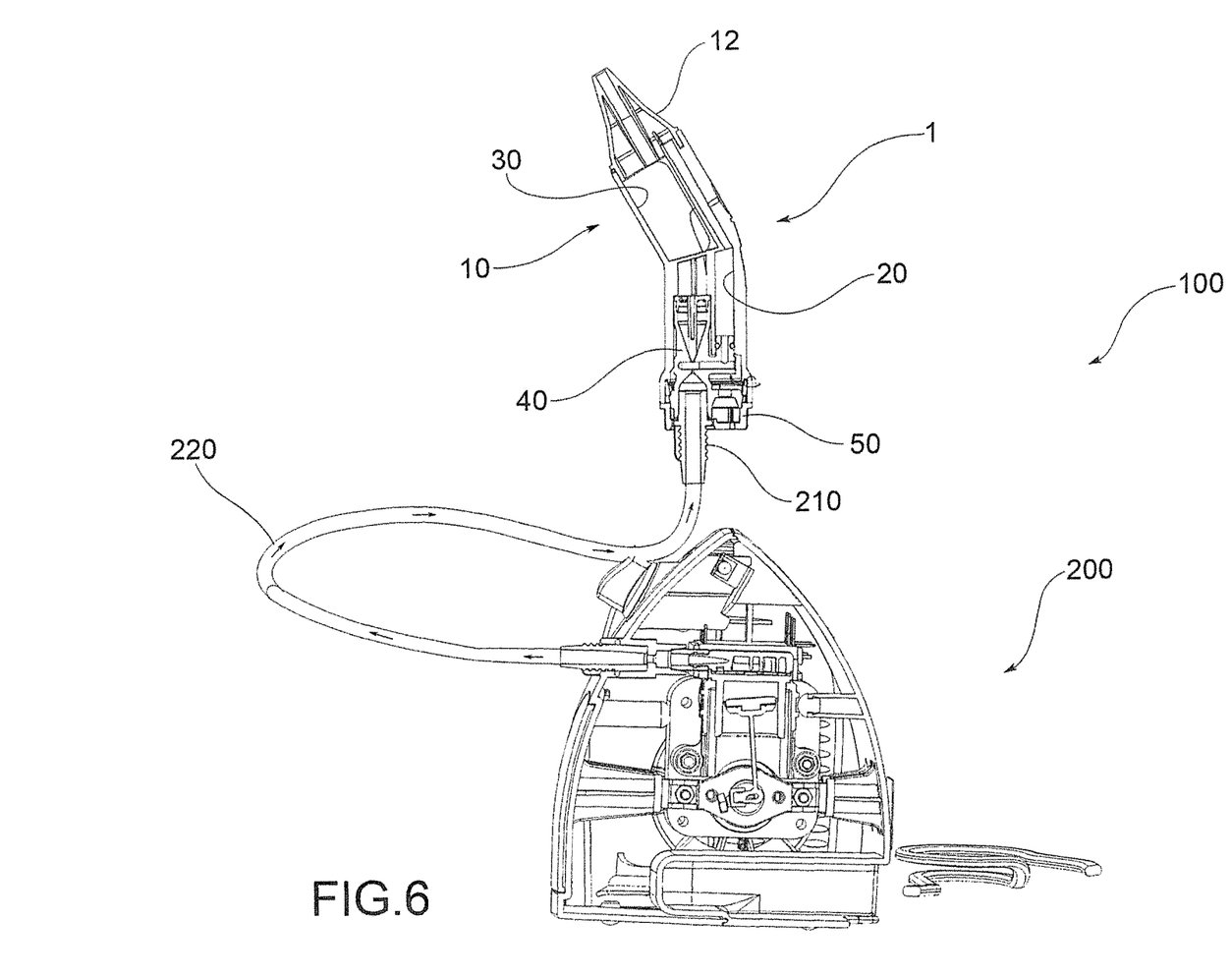
FIG. 6 is an axial schematic view of a nasal mucus aspirator according to the present invention.

The accessory according to the invention described thus allows realising a nasal mucus extractor 100, using a compressed air generator 200 suitable for generating a flow of compressed air at a pressure comprised, for example, between 0 and 10 bars, and a connection tube 220 provided with a fitting 210 for fluidically connecting the compressed air source 200 to the accessory 1.

Advantageously, for the compressed air generator 200 can use a compressor to perform usual aerosol therapy or nebulisation treatments.

Figure 8:
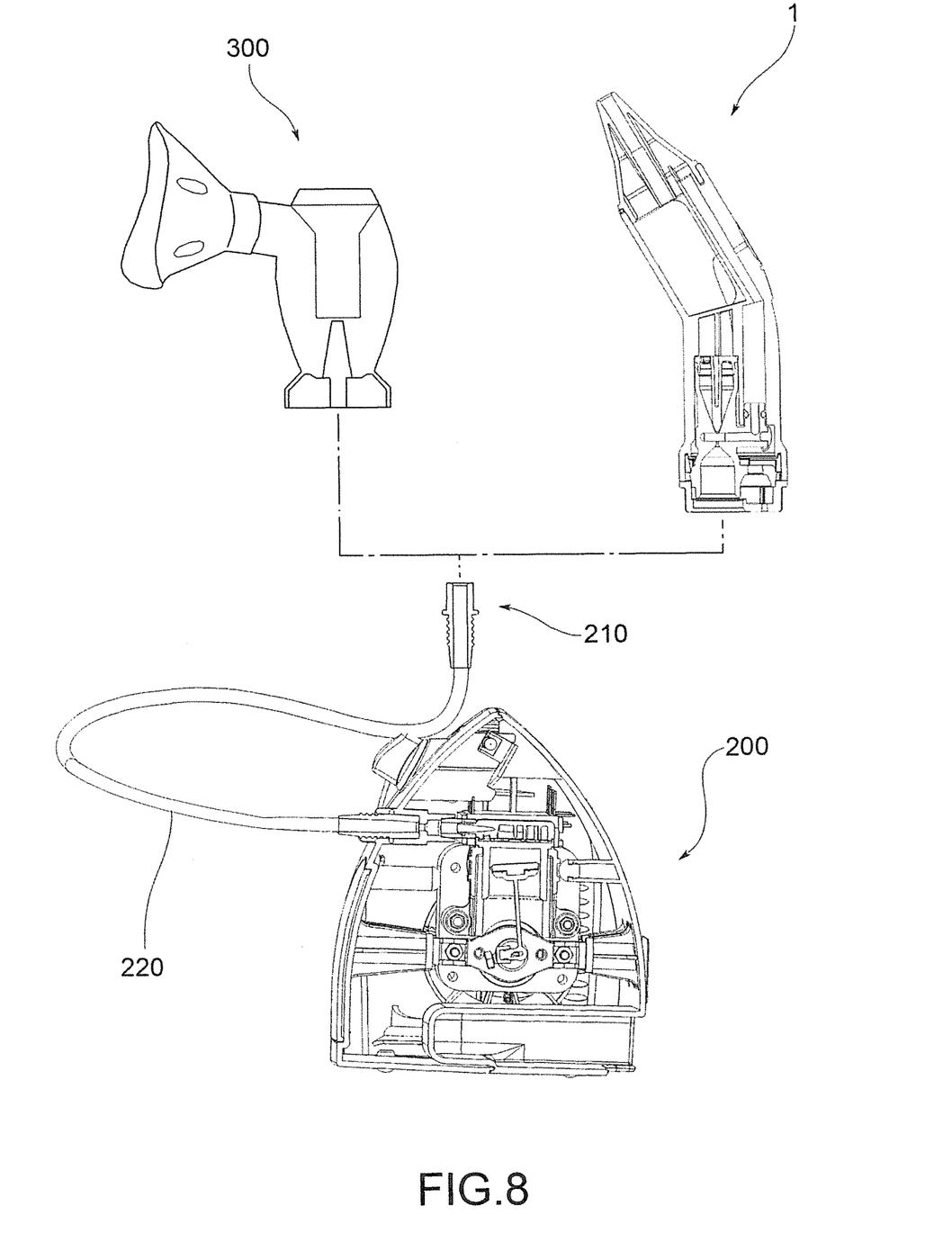
FIG. 8 is an example of a kit for the treatment of the upper respiratory system that uses the accessory according to the invention.

Therefore, the object of this invention is also a kit for the treatment of the upper respiratory tract, comprising a compressed air generator 200, an aspiration accessory 1 as described above, at least one further dispenser accessory 300 operating at a positive pressure generated by the compressed air generator 200 to dispense a nebulised medicinal substance in the nostrils and/or in the oral cavity, such as a mask for aerosol therapy or a nebuliser, and a connection tube 220 provided with a terminal fitting 210 for fluidically connecting the compressed air generator 200 to the aspiration accessory 1, or to at least a dispenser accessory 300.

The accessory and nasal mucus aspirator according to the invention allow achieving the predetermined purposes and advantages highlighted below.

The most stringent safety standards are complied with, since there is no contamination of the operator who performs the treatment or of the compressed air generator.

The aspiration of the mucus is performed with a predetermined negative pressure that is gentle on the patient. For example, with a compressor operating at a pressure of approximately to 5 bar, the Venturi effect obtains a negative pressure comprised between 0.1 to 1 bar, sufficient to delicately aspirate mucus from the nostrils of a child.

Thanks to the mucus inlet duct 14 which extends into the terminal nozzle 12, even in case of positive pressure in the accessory body 10, the aspirated mucus is prevented from returning towards the patient.

The structure of the accessory 1 is realised with a reduced number of components (for example 5 parts made of plastic and an O-ring), and is therefore reliable and inexpensive to produce.

The total cost of the nasal aspirator cost is reduced, since with only one compressor and connection tube, one can perform several functions: nasal aspirator, aerosol, nebuliser, etc. As noted above, the compressor operates in compression in exactly the same way to perform the various functions.

To the preferred embodiments of the mucus aspirator accessory according to the invention, a skilled person, to satisfy contingent requirements, may make modifications, adaptations and replacements of elements with others functionally equivalent, without departing from the scope of the following claims. Each of the characteristics described as belonging to a possible preferred embodiment can be achieved independently from the other preferred embodiments described.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. An accessory for a nasal mucous aspirator, the accessory comprising:
   an accessory body suitable to be gripped;
   in the accessory body, there being formed:
   a compressed air inlet passage suitable to be fluidically connected to a compressed air source to receive a flow of air at a positive pressure, said compressed air inlet passage defining a constriction so as to generate a Venturi effect;
   an aspiration passage flowing into said constriction and fluidically connected to a mucus inlet duct in such a way that, in said mucus inlet duct a negative pressure is generated by the Venturi effect suitable to aspirate the mucus,
   a mucus collection chamber formed in the accessory body which is in fluidic communication with the mucus inlet duct, wherein
   a terminal nozzle is placed at a distal end of said accessory body and is configured to be at least partially inserted into a nostril of a user, and the mucus inlet duct is formed in the terminal nozzle,
   the aspiration passage extends externally of the mucus collection chamber, and
   the aspiration passage has a distal portion that extends alongside of, and terminates distally beyond, a proximal end of the mucus inlet duct.

2. The accessory according to claim 1, wherein the compressed air inlet passage comprises a proximal end portion, suitable to be connected to the compressed air source, a distal portion in fluidic communication with an external environment, and the constriction between the proximal and distal portions, said constriction have a compressed air passage section at least less than the passage section of the proximal portion.

3. The accessory according to claim 1, wherein the mucus inlet duct extends from a distal end along a direction substantially rectilinear and has the proximal end facing an opening of the mucus collection chamber.

4. The accessory according to claim 1, wherein the compressed air inlet passage, and a proximal end portion of the aspiration passage are formed in a Venturi insert housed in an insert seat formed in the accessory body.

5. The accessory according to claim 4, wherein said Venturi insert comprises, aligned with each other along an insert longitudinal axis, a proximal portion defining a proximal portion of the compressed air inlet passage, and a distal portion defining a distal portion of the compressed air inlet passage, the Venturi insert also comprising an intermediate portion that defines a proximal portion of the aspiration passage flowing into the constriction.

6. The accessory according to claim 5, wherein said intermediate portion of the Venturi insert extends from the constriction along a transverse direction and terminates with a distal end sealingly inserted in an intermediate portion of the aspiration passage, formed in the accessory body.

7. The accessory according to claim 6, wherein the distal end of the intermediate portion of the Venturi insert is provided with an annular sealing element, the Venturi insert being removable from the insert seat through a proximal opening of the accessory body and being retained in said insert seat thanks to a calibrated interference between said annular sealing element and a side wall of the intermediate portion of the aspiration passage.

8. The accessory according to claim 2, wherein the proximal portion of the compressed air inlet passage is configured to be sealingly engaged by a fitting connected to a tube from the compressed air source.

9. The accessory according to claim 7, wherein to the proximal end of the accessory body is removably connected a ring nut having a bottom wall in which is formed a fitting opening aligned to the proximal portion of the compressed air inlet passage and suitable to allow the passage of the fitting through the ring nut, the Venturi insert being engaged by the ring nut in such a way that the removal of the Venturi insert from the insert seat is possible only after having disengaged the ring nut from the accessory body.

10. The accessory according to claim 9, wherein the Venturi insert comprises a ring nut coupling crown provided with a coupling member that engages a corresponding coupling counter-member formed in an annular portion of the ring nut.

11. The accessory according to claim 9, wherein the bottom wall of the ring nut is traversed by vent holes that fluidically connect the insert seat with an outside environment.

12. The accessory according to claim 2, wherein the constriction of the compressed air inlet passage is engaged by a pointed end of a peg positioned in the distal portion of the compressed air inlet passage.

13. A nasal mucus aspirator comprising:
   a compressed air generator configured to generate a flow of compressed air at a pressure comprised between 0 to 10 bar,
   an accessory according to claim 1, and
   a connection tube that fluidically connects the compressed air generator to the accessory.

14. A kit for the treatment of the upper respiratory tract comprising:
   a compressed air generator,
   an aspiration accessory according to claim 1,
   at least one further dispenser accessory operating at a positive pressure generated by the compressed air generator to dispense a nebulised medicinal substance in the nostrils and/or in the oral cavity, and a connection tube for fluidically connecting the compressed air generator to the aspiration accessory or to at least a dispenser accessory.

15. The accessory according to claim 1, wherein the aspiration passage communicates with an external environment through an actuation hole formed in a side wall of the accessory body.

16. The accessory according to claim 1, wherein the mucus collection chamber is formed at the distal end of the accessory body proximal to the terminal nozzle, and adjacent to the distal portion of the aspiration passage.

17. The accessory according to claim 1, wherein the mucus collection chamber is formed at the distal end of the accessory body proximal to the terminal nozzle.

18. The accessory according to claim 1, wherein the accessory body has a cylindrical lower portion and a cylindrical upper portion which is inclined with respect to the lower portion, when oriented in a vertical position of use.

19. The accessory according to claim 1, wherein the terminal nozzle is removably coupled to the accessory body by a calibrated interference, the calibrated interference being selected such that the terminal nozzle disengages from the accessory body when, in the accessory body, a positive pressure is generated higher than a predetermined threshold value.

20. A kit for the treatment of the upper respiratory tract, the kit comprising:
a compressed air generator; and an aspiration accessory, the aspiration accessory comprising:
an accessory body suitable to be gripped;
a terminal nozzle placed at a distal end of said accessory body and suitable to be at least partially inserted into a nostril of a user, a mucus inlet duct being formed in the terminal nozzle,
in the accessory body, there being formed:
a compressed air inlet passage suitable to be fluidically connected to a compressed air source to receive a flow of air at a positive pressure, said compressed air inlet passage defining a constriction so as to generate a Venturi effect;
an aspiration duct flowing into said constriction and fluidically connected to said mucus inlet duct in such a way that, in said mucus inlet duct a negative pressure is generated by the Venturi effect suitable to aspirate the mucus, wherein
the aspiration duct has a distal portion that extends alongside of, and terminates distally beyond, a proximal end of the mucus inlet duct; and
the kit further comprises at least one further dispenser accessory operating at a positive pressure generated by the compressed air generator to dispense a nebulised medicinal substance in the nostrils and/or in the oral cavity, and a connection tube for fluidically connecting the compressed air generator to the aspiration accessory or to at least a dispenser accessory.

* * * * *